United States Patent
Nishimura et al.

(10) Patent No.: US 10,988,452 B2
(45) Date of Patent: Apr. 27, 2021

(54) METHOD PRODUCING FOR 5-HYDROXYMETHYL-2-FURFURAL WITH SUPPRESSED BY-PRODUCT FORMATION

(71) Applicant: Nihon Shokuhin Kako Co., Ltd., Tokyo (JP)

(72) Inventors: Yuichi Nishimura, Shizuoka (JP); Hitoshi Takaguchi, Shizuoka (JP); Norihisa Hamaguchi, Shizuoka (JP)

(73) Assignee: Nihon Shokuhin Kako Co., Ltd., Tokyo (JP)

( * ) Notice: Subject to any disclaimer, the term of this patent is extended or adjusted under 35 U.S.C. 154(b) by 0 days.

(21) Appl. No.: 16/770,683

(22) PCT Filed: Dec. 7, 2018

(86) PCT No.: PCT/JP2018/045085
§ 371 (c)(1),
(2) Date: Jun. 8, 2020

(87) PCT Pub. No.: WO2019/112038
PCT Pub. Date: Jun. 13, 2019

(65) Prior Publication Data
US 2020/0399237 A1 Dec. 24, 2020

(30) Foreign Application Priority Data
Dec. 8, 2017 (JP) .............................. JP2017-235929

(51) Int. Cl.
*C07D 307/50* (2006.01)
(52) U.S. Cl.
CPC .................. *C07D 307/50* (2013.01)
(58) Field of Classification Search
CPC .................................................... C07D 307/50
See application file for complete search history.

(56) References Cited

U.S. PATENT DOCUMENTS

| 9,206,147 B2 * | 12/2015 | Cho ................ C07D 307/46 |
| 9,469,619 B2 * | 10/2016 | Lee ................ C07D 307/46 |
| 2019/0330172 A1 | 10/2019 | Nishimura et al. |

FOREIGN PATENT DOCUMENTS

| JP | H06504272 | 5/1994 |
| JP | 2007-277198 | 10/2007 |
| JP | 2013-203665 | 10/2013 |
| WO | 2018003295 | 1/2018 |

OTHER PUBLICATIONS

International Search Report in corresponding PCT/JP2018/045085, dated Feb. 12, 2019 (English translation attached).
Vinke, et al., "The Dehydration of Fructose Towards 5-Hydroxymethylfurfural Using Activated Carbon as Adsorbent", Starch/Staerke, 1992, 44(3), pp. 90-96.
Kilic, et al., "Fructose Dehydration to 5-Hydroxymethylfurfural over Sulfated TiO2—SiO2, Ti-SBA-15, ZrO2, SiO2, and Activated Carbon Catalysts", Ind. Eng. Chem. Res. 2015, 54, 19, pp. 5220-5225.
Wang, et al., "Efficient catalytic conversion of fructose into hydroxymethylfurfural by a novel carbon-based solid acid", Green Chem., 2011,13, pp. 2678-2681.
Yang, et al., "Dehydration of Fructose into 5-Hydroxymethylfurfural Catalyzed by Phosphorylated Activated Carbon Catalyst", Asian Journal of Chemistry Aug. 2015 27(8), pp. 2979-2982.
Qi, et al., "Acid-catalyzed Dehydration of Fructose Into 5-hydroxymethylfurfural by Cellulose-Derived Amorphous Carbon", ChemSusChem Nov. 2012;5(11), pp. 2215-2220.
Liu, et al., "Conversion of fructose into 5-hydroxymethylfurfural and alkyl levulinates catalyzed by sulfonic acid-functionalized carbon materials", Green Chem., 2013,15, pp. 2895-2903.
Russo, et al., "Solid acids with SO3H groups and tunable surface properties: versatile catalysts for biomass conversion", J. Mater. Chem. A, 2014, 2, pp. 11813-11824.
Fabicovicova, et al., "Hydrogenolysis of cellulose to valuable chemicals over activated carbon supported mono- and bimetallic nickel/tungsten catalysts", Green Chem., 2014,16, pp. 3580-3588.
International Preliminary Report on Patentability in corresponding PCT/JP2018/045085, dated Jun. 9, 2020 (English translation attached).

* cited by examiner

*Primary Examiner* — Golam M Shameem
(74) *Attorney, Agent, or Firm* — Hovey Williams LLP

(57) ABSTRACT

An object of the present invention is to provide a method for producing 5-hydroxymethyl-2-furfural (5-HMF) with suppressed production of byproducts. The present invention provides a method for producing 5-HMF, comprising the step of performing a dehydration reaction of a carbohydrate comprising a hexose as a constituent sugar or a derivative thereof to produce 5-hydroxymethyl-2-furfural, wherein the dehydration reaction is performed in the presence of activated carbon. The present invention also provides a method for producing a carbohydrate composition comprising 5-hydroxymethyl-2-furfural, comprising the step of heating a carbohydrate composition comprising one or more selected from the group consisting of a carbohydrate comprising a hexose as a constituent sugar and a derivative thereof, in the presence of an acid catalyst and activated carbon at a temperature of 90 to 400° C.

3 Claims, 3 Drawing Sheets

METHOD PRODUCING FOR 5-HYDROXYMETHYL-2-FURFURAL WITH SUPPRESSED BY-PRODUCT FORMATION

CROSS-REFERENCE TO RELATED APPLICATIONS

The present application is the U.S. National Stage of International Patent Application No. PCT/JP2018/045085, filed Dec. 7, 2018, which claims the benefit of priority from the prior Japanese Patent Application No. 2017-235929 filed on Dec. 8, 2017, the entire disclosures of which are incorporated herein by reference.

TECHNICAL FIELD

The present invention relates to a method for producing 5-hydroxymethyl-2-furfural (5-hydroxymethyl-2-furaldehyde, hereinafter abbreviated as "5-HMF" in some cases) with suppressed production of byproducts. The present invention also relates to an agent for suppressing the production of byproducts and a method for suppressing the production of byproducts, in the production of 5-HMF.

BACKGROUND ART

To establish a sustainable circulating society, the utilization of biomass which is a renewable organism-derived resource is attracting attention. As the utilization of biomass, 5-HMF, which is a product obtained by dehydration of a carbohydrate, is attracting attention. 5-HMF is known as a compound contained in foods such as honey, and the utilization thereof as a raw material for polymers, plastics and biofuels is contemplated. In particular, plastics prepared from biomass are referred to as bioplastics. In recent years, 100% bio-based polyethylene furanoate (PEF) is expected as a novel bioplastic. PEF is a condensation polymer of 2,5-furandicarboxylic acid and ethylene glycol. Produced is 2,5-furandicarboxylic acid (hereinafter abbreviated as "FDCA" in some cases) via an oxidation reaction of 5-HMF.

It is known that 5-HMF can be produced through an intramolecular dehydration reaction using, for example, fructose having a hexose skeleton as a raw material by an acid catalyst. As the acid catalyst for this reaction, inorganic acids such as hydrochloric acid, sulfuric acid and phosphoric acid and solid acid catalysts such as strongly acidic cation exchange resins, metal oxides and immobilized sulfuric acid catalysts are used (Patent Documents 1 and 2). A method using any of such catalysts can be used to produce 5-HMF, but the applicable raw material concentration is limited for reasons such as reduction in selectivity. Further, the solid acid catalyst is advantageous in that it can be easily removed later by filtration, centrifugation or the like after the reaction when 5-HMF is produced on an industrial scale, but involves the problems of expensiveness and difficulty in obtainment on an industrial scale. Further, when 5-HMF is inexpensively produced with a high yield on an industrial scale, it is indispensable to increase the raw material concentration. However, the above method causes production of large amounts of insoluble byproducts which are attached to a producing device, leading to the problem of difficulty in continuous production.

REFERENCE LIST

Patent Documents

Patent Document 1: JP 2013-203665 A
Patent Document 2: JP H6-504272 T

SUMMARY OF THE INVENTION

An object of the present invention is to provide a method for producing 5-HMF with suppressed production of byproducts. Another object of the present invention is to provide an agent for suppressing the production of byproducts and a method for suppressing the production of byproducts, in the synthesis of 5-HMF.

The present inventors have found that it is possible to produce a carbohydrate composition comprising 5-HMF while suppressing the production of insoluble byproducts, by adding activated carbon when subjecting, to heating reaction treatment, a carbohydrate composition comprising fructose in the presence of an acid catalyst. Further, the present inventors have found that the heating reaction suppresses the attachment of insoluble byproducts to a reaction device and ensures continuous use of producing facilities, and that the reaction product has a low degree of coloration. The present invention is based on these findings.

The present invention provides the following inventions.

[1] A method for producing 5-hydroxymethyl-2-furfural, comprising the step of performing a dehydration reaction of a carbohydrate comprising a hexose as a constituent sugar or a derivative thereof to produce 5-hydroxymethyl-2-furfural, wherein the dehydration reaction is performed in the presence of activated carbon.

[2] The method according to [1], wherein the carbohydrate or derivative thereof has a solid content concentration of 15% by mass or more.

[3] The method according to [1] or [2], wherein the dehydration reaction is a reaction using an acid catalyst.

[4] A method for producing a carbohydrate composition comprising 5-hydroxymethyl-2-furfural, comprising the step of heating a carbohydrate composition comprising one or more selected from the group consisting of a carbohydrate comprising a hexose as a constituent sugar and a derivative thereof, in the presence of an acid catalyst and activated carbon at a temperature of 90 to 400° C.

[5] The method according to [4], wherein the carbohydrate composition has a solid content concentration of 15% by mass or more.

[6] An agent for suppressing the production of byproducts in a reaction for producing 5-hydroxymethyl-2-furfural, through a dehydration reaction, from a carbohydrate comprising a hexose as a constituent sugar or a derivative thereof, the agent for suppressing the production of byproducts comprising activated carbon.

[7] The agent for suppressing the production of byproducts according to [6], which is intended for use in a reaction system in which the carbohydrate or derivative thereof has a solid content concentration of 15% by mass or more.

[8] The agent for suppressing the production of byproducts according to [6] or [7], wherein the dehydration reaction is a reaction using an acid catalyst.

[9] A method for suppressing the production of byproducts in a reaction for producing 5-hydroxymethyl-2-furfural, through a dehydration reaction, from a carbohydrate comprising a hexose as a constituent sugar or a derivative thereof, wherein the dehydration reaction is performed in the presence of activated carbon.

[10] The method for suppressing the production of byproducts according to [9], wherein the carbohydrate or derivative thereof has a solid content concentration of 15% by mass or more.

[11] The method for suppressing the production of byproducts according to [9] or [10], wherein the dehydration reaction is a reaction using an acid catalyst.

[12] Use of activated carbon as an agent for suppressing the production of byproducts in a reaction for producing 5-hydroxymethyl-2-furfural, through a dehydration reaction, from a carbohydrate comprising a hexose as a constituent sugar or a derivative thereof, or in a method for suppressing the production of byproducts in a reaction for producing 5-hydroxymethyl-2-furfural, through a dehydration reaction, from a carbohydrate comprising a hexose as a constituent sugar or a derivative thereof.

[13] The use according to [12], wherein the dehydration reaction is a reaction using an acid catalyst.

The methods [1] and [4] are sometimes referred to collectively as "production method of the present invention" herein.

The present invention provides a method for producing 5-HMF with suppressed production of byproducts, using activated carbon. Activated carbon is a relatively inexpensive raw material and can be readily removed outside the system by solid-liquid separation, and thus is advantageous in that 5-HMF with reduced byproduct production can be simply and inexpensively produced on an industrial scale according to the production method of the present invention. The 2,5-furandicarboxylic acid produced from 5-HMF serves as a substitute for terephthalic acid as a raw material for polyethylene terephthalate and is used as a raw material for polyethylene furanoate. Thus, the present invention can be said to be very advantageous in that the invention enables substitution of a petrochemical product PET resin by a resin comprising, as a raw material, biomass which is a renewable resource.

DETAILED DESCRIPTION OF THE INVENTION

Figure 1:
FIG. 1 is a photograph showing a state of a reaction vessel washed with water three times after a reaction using hydrochloric acid as an acid catalyst (Example 1 and Reaction Product 11).

The production method of the present invention is characterized by performing an intramolecular dehydration reaction from a carbohydrate comprising a hexose as a constituent sugar into 5-HMF in the presence of activated carbon. The dehydration reaction is performed in the presence of activated carbon, thereby making it possible to suppress the byproduct production.

As the "activated carbon" used in the present invention, a product known as a porous carbonaceous adsorbent can be employed. Activated carbon can mainly be obtained by carbonizing, through heat treatment, a natural carbonaceous material derived from an animal/plant or a mineral, such as coal, coke, pitch, bone charcoal, wood charcoal, coconut shell, wood, sawdust, lignin or bovine bone; an organic polymer such as a synthetic resin, e.g., a phenol resin or polyacrylonitrile; and a carbonaceous material such as soot, and activating the carbonized material.

The "activated carbon" used in the present invention may be either activated carbon itself or a material partially containing activated carbon. Examples of the material partially containing activated carbon include those having activated carbon attached onto a carrier such as a plastic, a mineral, a ceramic or a fiber; those prepared by granulating powdered activated carbon with a pressure-sensitive adhesive; and those granulated from powdered activated carbon and a powder of a mineral, a ceramic or the like. Bone charcoal, wood charcoal, graphite, carbon black and the like may be used as the materials partially containing activated carbon in their structure in the present invention.

The "activated carbon" used in the present invention may be modified activated carbon. For example, it is also possible to use activated carbon in which carboxyl groups are introduced by oxidation reaction treatment with hydrogen peroxide or nitric acid or through air oxidation (heat treatment), and activated carbon in which sulfone groups are introduced by sulfonation treatment with sulfuric acid or fuming sulfuric acid. Alternatively, activated carbon preliminarily immersed in an acidic solution may be used as it is or after being washed. However, commercial activated carbon itself has a sufficient function as an agent for suppressing the production of byproducts as is evident from the Examples which will be described later, and thus the activated carbon used in the present invention is preferably activated carbon which is not subjected to modification treatment, i.e., unmodified activated carbon, in consideration of its economy, easiness of acquisition and the like.

The "activated carbon" used in the present invention may have a metal carried thereon. That is, the activated carbon subjected to carrying treatment in the present invention refers to activated carbon which, itself, serves as a carrier and has a metal useful as a catalyst carried on its surface. The metal to be carried on the activated carbon is not particularly limited, and examples thereof include Nb, Ti, Ni and Pd. However, commercial activated carbon itself has a sufficient function as an agent for suppressing the production of byproducts as is evident from the Examples which will be described later, and thus the activated carbon used in the present invention is preferably activated carbon which is not subjected to carrying treatment, i.e., non-carrying activated carbon, in consideration of its economy, easiness of acquisition and the like.

The shape of the activated carbon used in the present invention is not particularly limited, and examples thereof include granular, powdery, fibrous, sheet-like, and honeycomb-like shapes. Specific examples of the activated carbon used in the present invention include powdered carbons such as steam activated carbon, zinc chloride activated carbon and phosphoric acid activated carbon; and granular carbons such as crushed carbon, granulated carbon, granulated carbon and spherical carbon.

When using the powdered activated carbon as the activated carbon used in the present invention, for example, it is possible to use "Shirasagi A, Shirasagi C, and Purified Shirasagi" manufactured by Japan Enviro Chemicals, Ltd.; "Taiko A, Taiko S, Taiko SA1000, and Taiko Y" manufactured by FUTAMURA CHEMICAL CO., LTD; and "CA, CAP, and CASP" manufactured by Norit Japan Co., Ltd. When using the granular activated carbon, for example, it is possible to use "Granular Shirasagi WH and Granular Shirasagi C" manufactured by Japan Enviro Chemicals. Ltd.; "F400, F300, PCB, BPL, CAL, CPG, and APC" manufactured by Toyo Calgon Co., Ltd.; "Kuraray Coal KW" manufactured by KURARAY CHEMICAL CO., LTD.; "BAC" manufactured by KUREHA CHEMICAL INDUSTRY CO., LTD.; and "PN, ZN, SA, SA-SW, SX, CN, CG, D-10, W, GL, and HB PLUS" manufactured by Norit Japan Co., Ltd. When using the fibrous activated carbon, it is possible to use "FX-300" manufactured by Toyo Rayon Co., Ltd.; "M-30" manufactured by Osaka Gas Co., Ltd.; and "KF-1500" manufactured by TOYOBO CO., LTD. When using the sheet-like activated carbon, it is possible to use "Microlite AC" manufactured by Kanebo, Ltd.

The amount of the activated carbon used in the production method of the present invention is not specifically limited as long as the function as the agent for suppressing the production of byproducts is exerted, and can be adjusted in a range of 0.01 to 1.0 part by mass, and preferably 0.03 to 0.3 parts by mass or 0.01 to 0.1 parts by mass, based on 1 part by mass of a raw material carbohydrate (per solid content).

In the production method of the present invention, the dehydration reaction for producing 5-HMF from a carbohydrate comprising a hexose as a constituent sugar or a derivative thereof can be performed using an acid catalyst.

The acid catalyst in the production method of the present invention is not particularly limited, and usable examples thereof include inorganic acids (e.g., phosphoric acid, hydrochloric acid, boric acid, nitric acid, and sulfuric acid), organic acids (e.g., citric acid, acetic acid, trifluoroacetic acid, oxalic acid, lactic acid, pyruvic acid, levulinic acid, formic acid, fumaric acid, maleic acid, glutaric acid, itaconic acid, phthalic acid, isophthalic acid, terephthalic acid, and p-toluenesulfonic acid), strongly acidic cation exchange resins (e.g., Amberlyst, Amberlite, and Diaion), metal oxides (e.g., niobia, titania, alumina, zeolite, and silica), immobilized catalysts (e.g., sulfated zirconia and phosphorylated titania), and metal salts (e.g., chromium chloride, aluminum chloride, and zinc chloride). In the production method of the present invention, one acid catalyst may be used, or two or more acid catalysts may be used in combination.

The amount of the acid catalyst used in the production method of the present invention is not specifically limited as long as the intramolecular dehydration reaction of the raw material carbohydrate progresses, and can be adjusted in a range of 0.001 to 1.0 part by mass, and preferably 0.002 to 0.3 parts by mass or 0.003 to 0.1 parts by mass, based on 1 part by mass of the raw material carbohydrate (per solid content).

A part of the produced 5-HMF is sometimes adsorbed on the activated carbon in the production method of the present invention. However, the 5-HMF adsorbed on the activated carbon can also be recovered by washing the activated carbon with water, an organic solvent or the like in order to improve the yield.

The activated carbon used in the present invention is preferred because of its low cost as a solid material and additionally its less risk in view of sanitation and high safety in handling, or even when it remains in the product. The activated carbon can be easily separated from the reaction system by sedimentation, filtration, centrifugation, or use in the form of a packed column, and thus is easy to handle.

The activated carbon is also preferred in view of economy since it is excellent in reusability and can be repeatedly used. The method of reusing the activated carbon of the present invention can be an existing method and is not specifically limited. For example, it is possible to use a vacuum regeneration method in which an adsorbate is desorbed by decreasing the solute concentration of a solvent and pressure; a solvent regeneration method involving extraction with a solvent; a substitution regeneration method involving substitution with any other adsorbate; a heat desorption method by heating; a chemical regeneration method by chemical treatment; and an oxidative decomposition regeneration method by oxidation and decomposition.

The method for producing 5-HMF of the present invention is characterized by using, as a raw material, a carbohydrate comprising a hexose as a constituent sugar or a derivative thereof. The carbohydrate used as a raw material may be a hexose itself (monosaccharide) or a sugar polymer (oligosaccharide or polysaccharide) comprising a hexose as a constituent sugar. Examples of the hexose include fructose, glucose, galactose, mannose, psicose, sorbose, and tagatose. In consideration of the economy, easiness of acquisition and the like, fructose and glucose are preferred, and fructose is especially preferred. The sugar polymer comprising a hexose as a constituent sugar is not particularly limited. Examples of the sugar polymer include mannobiose, lactose, lactulose, mannan, galactan, arabinogalactan, and xyloglucan. In consideration of the economy, a sugar polymer comprising a hexose as a constituent sugar is preferably used. In consideration of the economy, easiness of acquisition and the like, a sugar polymer comprising fructose and/or glucose as a constituent sugar is more preferred, and examples thereof include sucrose, maltose, trehalose, turanose, isomaltulose, cellobiose, isomaltose, nigerose, maltulose, isomaltulose, gentiobiose, maltotriose, 1-kestose, maltooligosaccharide, fructooligosaccharide, dextrin, dextran, inulin, levan, starch (e.g., corn starch), and cellulose. Sucrose, inulin and starch are particularly preferred. When a sugar polymer comprising a hexose as a constituent sugar is used as a raw material carbohydrate, it is possible to further convert the carbohydrate into 5-HMF through an intramolecular dehydration reaction using an acid catalyst simultaneously or sequentially while supplying the hexose through decomposition of the carbohydrate at the time of a heating reaction.

The derivative of the carbohydrate is not particularly limited as long as it has a functional group such as a hydroxyl group to be subjected to the dehydration reaction, and examples thereof include modified sugars such as amino sugar, etherified sugar, halogenated sugar and phosphorylated sugar. Examples of such derivatives include glucosamine, glucose-6-phosphoric acid, and methyl α-D-mannopyranoside.

As the raw material carbohydrate of the present invention, fructose and/or glucose are preferably used in view of their reactivity, easiness of obtainment, price, and the like, and fructose is more preferably used. The raw material carbohydrate of the present invention may be a pure product, but can also be a carbohydrate composition which is a mixture of a plurality of carbohydrates. When the carbohydrate composition is used as a raw material carbohydrate for the production method of the present invention, the carbohydrate composition preferably contains fructose in an amount of 10% by mass or more per solid content, more preferably contains fructose in an amount of 30% by mass or more per solid content.

The nature of the carbohydrate which serves as the raw material for the production method of the present invention is not particularly limited as long as the reaction progresses. The carbohydrate may be in the form of a crystal, non-crystalline powder or solution, but is preferably in the form of a solution from the viewpoint of reaction efficiency and economy. Briefly, the production method of the present invention can be carried out preferably in a solution. The solid content concentration of the raw material carbohydrate solution can be set to 1% by mass to 85% by mass, preferably 5% by mass to 80% by mass or 20% by mass to 75% by mass. In the production method of the present invention, the byproduct production can effectively be suppressed also by increasing the concentration of the carbohydrate which serves as a substrate. Therefore, the solid content concentration (or substrate concentration) of the raw material carbohydrate solution in the production method of the present invention can be set to 15% by mass or more (for example, 15% by mass to 90% by mass), preferably 20% by mass or more (for example, 20% by mass to 90% by mass), more preferably 30% by mass or more (for example, 30% by mass to 90% by mass), particularly preferably 40% by mass or more (for example, 40% by mass to 90% by mass).

The solvent constituting the reaction solution used in the production method of the present invention is also not particularly limited, and examples thereof include water; organic solvents such as ethanol, methanol, isopropanol, acetone, acetonitrile, methyl isobutyl ketone, and dimethyl sulfoxide; and ion liquids such as 1-butyl-3-methylimidazolium tetrafluoroborate and 1-butyl-3-methylimidazolium hexafluorophosphate. These solvents may be used singly or mixed in any ratio for use. In consideration of the reaction efficiency and the like, an organic solvent is preferably used as the solvent. In consideration of the cost, safety and the like, water (aqueous solution) is preferably used as the solvent. Also, in consideration of the price, easiness of obtainment and the like, a high fructose corn syrup (fructose glucose syrup, glucose fructose syrup, or high-fructose syrup) is particularly suitable as the raw material for the production method of the present invention.

Any reaction conditions may be employed in the production method of the present invention as long as 5-HMF is produced through an intramolecular dehydration reaction. From the viewpoint of efficient production of 5-HMF from fructose, for example, the reaction temperature (product temperature of the raw material carbohydrate) can be set to 90 to 400° C. (preferably 100 to 400° C., more preferably 110 to 250° C., further preferably 110 to 200° C., particularly preferably 120 to 180° C., most preferably 130 to 170° C.), and the reaction time can be set to 0.2 to 10 hours (preferably 0.5 to 6 hours, more preferably 1 to 4 hours).

The reaction temperature and reaction time can be appropriately adjusted. For example, the reaction time can be shortened since the concentration of 5-HMF can be increased quickly by increasing the reaction temperature. On the other hand, the reaction temperature can be decreased since the concentration of 5-HMF can be increased by prolonging the reaction time.

The reaction conditions are appropriately set as described above, so that the production method of the present invention can serve as a method for producing a carbohydrate composition comprising, for example, 5% by mass or more of 5-HMF per solid content of the composition. In the production method of the present invention, a method for producing a carbohydrate composition comprising preferably 7% by mass or more of 5-HMF per solid content of the composition, more preferably 10% by mass or more of 5-HMF per solid content of the composition can be used.

The pressure at the reaction is also not particularly limited in the production method of the present invention, and the reaction may be performed under any of normal pressure conditions, pressurization conditions and reduced pressure conditions, but, from the viewpoint of the reaction efficiency, is performed preferably under pressurization conditions, more preferably under the pressure conditions of 1 to 9 $kgf/cm^2$. The reaction is performed under the pressurization conditions, thereby making it possible to further reduce the production of a sugar condensate.

In the production method of the present invention, the 5-HMF obtained by the dehydration reaction or a composition comprising the 5-HMF can be used as it is for that purpose. According to need, the reaction product may be, for example, centrifuged or filtered to remove insoluble matter and then subjected to resin fractionation, distillation separation or extraction treatment with a solvent.

As will be described in the Examples below, a carbohydrate composition comprising 5-HMF can be produced by subjecting a carbohydrate composition comprising a carbohydrate comprising at least a hexose as a constituent sugar to heating treatment in the presence of an acid catalyst and activated carbon. Thus, according to another aspect of the present invention, there is provided a method for producing a carbohydrate composition comprising 5-HMF by heating a carbohydrate composition comprising one or more selected from the group consisting of carbohydrates comprising a hexose as a constituent sugar and derivatives thereof, in the presence of an acid catalyst and activated carbon, at a temperature of 90° C. to 400° C. This production method can be carried out according to the above descriptions about the production method of the present invention.

The production method of the present invention reduces the byproduct production that may generate through a heating reaction to improve the yield as a result. The production method of the present invention also suppresses the attachment of insoluble byproducts to a reaction device, and ensures continuous use of producing facilities. The production method of the present invention also ensures the production of a reaction product having a low degree of coloration. Namely, the production method of the present invention is advantageous in that 5-HMF with a high commercial value can be continuously produced with a high yield.

Further, the production method of the present invention can effectively suppress the byproduct production even when the substrate concentration is increased in the production of 5-HMF. Accordingly, the production method of the present invention is advantageous in that 5-HMF can be produced with a high yield on an industrial scale.

The 5-HMF obtained by the production method of the present invention can be utilized as a raw material for biofuels or a raw material for resins such as biomass plastics.

Examples of the resin made from 5-HMF as a raw material or an intermediate for its production include polyethylene furanoate and 2,5-furandicarboxylic acid.

Namely, the present invention provides a method for producing 2,5-furandicarboxylic acid or an ester thereof, comprising subjecting the 5-HMF obtained by the production method of the present invention to an oxidation reaction to obtain 2,5-furandicarboxylic acid, and optionally esterifying the 2,5-furandicarboxylic acid. The method comprising subjecting 5-HMF to an oxidation reaction to produce 2,5-furandicarboxylic acid is known to those skilled in the art, and can be carried out with reference to the descriptions of WO 2008/054804, JP 2015-83559 A, JP 2008-88134 A and the like. As an example, 2,5-furandicarboxylic acid can be produced by oxidizing 5-HMF in the presence of a metal catalyst (for example, platinum, palladium, bismuth, tin, rhenium, copper, silver, magnesium or manganese). This oxidation reaction can be carried out, for example, at a temperature of 30° C. to 180° C. and a pressure of 1.0 kgf/cm$^2$ to 16.3 kgf/cm$^2$. Also, the esterification of 2,5-furandicarboxylic acid can be performed according to a normal method. Examples of esters of 2,5-furandicarboxylic acid include esters thereof with a volatile alcohol or phenol, and methyl esters and ethyl esters are preferred.

Also, the present invention provides a method for producing a copolymer, comprising the steps of subjecting, to an oxidation reaction, the 5-HMF obtained by the production method of the present invention to obtain 2,5-furandicarboxylic acid or an ester thereof, and copolymerizing the 2,5-furandicarboxylic acid or ester thereof with a different copolymerizable monomer. The copolymerizing step can be carried out by conducting a transesterification reaction or esterification reaction to obtain a prepolymer (lower polymer), and then subjecting the prepolymer to a polycondensation reaction to obtain a high-molecular-weight copolymer. The copolymerizing step can also be carried out by subjecting a copolymerizable monomer comprising 2,5-furandicarboxylic acid or an ester thereof to a polycondensation reaction to obtain a high-molecular-weight copolymer. Here, the transesterification reaction refers to the step of transesterifying the carboxylic acid ester which constitutes the copolymer of the present invention with an alcohol component at a predetermined temperature to obtain a prepolymer. The esterification reaction refers to the step of esterifying the carboxylic acid component which constitutes the copolymer of the present invention with an alcohol component at a predetermined temperature to obtain a prepolymer. The polycondensation reaction refers to the step of subjecting the prepolymer obtained by the transesterification or esterification reaction or a copolymerizable monomer to pressure reduction treatment to initiate a polymerization reaction, thereby obtaining a high-molecular-weight copolymer.

Examples of the different copolymerizable monomer that can be used in the production method of the present invention include compounds having two or more hydroxyl groups. The copolymerizable monomer is preferably a diol compound or polyol compound, more preferably ethylene glycol and 1,4-butanediol. When ethylene glycol is used as the different copolymerizable monomer in the production method of the present invention, the final product copolymer (resin composition) is polyethylene furanoate. In the production method of the present invention, a diol such as diethylene glycol, propylene glycol, 1,3-propanediol, 1,4-butanediol, 1,5-pentanediol, cyclobutanedimethanol, cyclohexanedimethanol, 2,5-furandimethanol or isosorbide can be used as the different copolymerizable monomer to obtain a copolymer. A method comprising subjecting 2,5-furandicarboxylic acid or an ester thereof to a copolymerization reaction (polycondensation reaction) with a copolymerizable monomer (especially, ethylene glycol), thereby producing a copolymer (especially, polyethylene furanoate) is known to those skilled in the art. For example, the method can be carried out with reference to the descriptions of WO 2010/077133, JP 2015-506389 T and the like. As an example, polyethylene furanoate (PEF) can be produced by subjecting an ester of 2,5-furandicarboxylic acid and ethylene glycol to a transesterification reaction using titanium (IV) isopropoxide (Ti[OCH(CH$_3$)$_2$]$_4$) and antimony oxide (III) (Sb$_2$O$_3$) as catalysts, and then polycondensing the transesterification product under a reduced pressure. The transesterification reaction can be carried out at 150° C. to 220° C., and the polycondensation reaction can be carried out within a temperature range between the melting point of the copolymer and a temperature 30° C. higher than the melting point (but about 180° C. or higher) under a high vacuum.

The 5-HMF or derivative thereof obtained by the production method of the present invention can be utilized, for example, as a fragrance imparting component, a physiologically active component, a food raw material, and a pharmaceutical raw material (for example, JP 2015-211669 A, JP 2008-193933 A, JP 2006-508998 T, JP 2010-248107 A and JP 2011-136959 A). The activated carbon used as the catalyst has been confirmed to be safe to humans, as can be understood from the fact that it has been utilized as a food additive. Therefore, the produced 5-HMF or derivative thereof is advantageous in that it can be applied as it is as a food or pharmaceutical raw material. Namely, the present invention provides a method for producing a pharmaceutical or food product, comprising carrying out the production method of the present invention to produce 5-HMF, optionally derivatizing the obtained 5-HMF, and blending the obtained 5-HMF or derivative thereof to a pharmaceutical or food raw material. The method for producing a pharmaceutical or food product can be carried out according to normal procedures for producing a pharmaceutical or food product except the step of blending the 5-HMF or derivative thereof, of course. Examples of the derivative of 5-HMF include 5-methoxymethyl-2-furfural, and the derivative can be produced, for example, according to the descriptions of JP 2010-538033 T.

The 5-HMF or derivative thereof obtained by the production method of the present invention can also be used as a raw material for synthesis of a pharmaceutical product. For example, 5-HMF is admitted as a sovereign medicine for sickle cell disease by the United States Food and Drug Administration (FDA).

The present invention provides an agent for suppressing the production of byproducts in a reaction for producing 5-HMF, through a dehydration reaction, from a carbohydrate comprising a hexose as a constituent sugar, the agent for suppressing the production of byproducts comprising activated carbon. The agent for suppressing the production of byproducts of the present invention can be used in a method for producing 5-HMF by subjecting a carbohydrate raw material comprising a hexose as a constituent sugar, such as fructose, to a dehydration reaction, as described in the production method of the present invention. The agent for suppressing the production of byproducts according to the present invention can be carried out according to the descriptions about the production method of the present invention. While the byproducts are attached to a reaction vessel, and thus greatly affect the production process, the agent for suppressing the production of byproducts of the present invention can suppress the production and attachment of the byproducts, and thus can also be used as an agent for suppressing the attachment of byproducts to a reaction vessel.

The present invention also provides a method for suppressing the production of byproducts in a reaction for producing 5-hydroxymethyl-2-furfural, through a dehydration reaction, from a carbohydrate comprising a hexose as a constituent sugar or a derivative thereof, wherein the dehydration reaction is performed in the presence of activated carbon. The method of the present invention can be carried out according to the descriptions about the production method of the present invention and the agent for suppressing the production of byproducts of the present invention.

The present invention also provides use of activated carbon as an agent for suppressing the production of byproducts in a reaction for producing 5-hydroxymethyl-2-furfural, through a dehydration reaction, from a carbohydrate comprising a hexose as a constituent sugar or a derivative thereof, or in a method for suppressing the production of byproducts in a reaction for producing 5-hydroxymethyl-2-furfural, through a dehydration reaction, from a carbohydrate comprising a hexose as a constituent sugar or a derivative thereof. The use of the present invention can be carried out according to the descriptions about the production method of the present invention, the agent for suppressing the production of byproducts of the present invention, and the method for suppressing the production of byproducts of the present invention.

EXAMPLES

Hereinafter, the present invention will be described in more detail by way of the following examples, but is not limited thereto. Unless otherwise noted herein, the unit "%" represents % by mass, and, when reference is made to the proportion (content) per "solid content" or the content proportion (concentration) of the "solid content," it means a proportion defined based on the mass of the solid component.

Example 1: Production of 5-HMF Using Agent for Suppressing the Production of Byproducts, and Analysis Thereon (1) Preparation of Samples In the present example, a high fructose syrup (fructose content per solid content: 95%; solid content concentration: 75.7%; product name: L-95; manufactured by Nihon Shokuhin Kako Co., Ltd.) was used as a substrate carbohydrate. The substrate carbohydrate (1.4 g (carbohydrate mass)) was put in respective reaction vessels (made of stainless steel), and activated carbon 1 (zinc chloride activated carbon) as an agent for suppressing the production of byproducts and various catalysts were added so as to attain the amounts (ratio % with respect to the solid content of the substrate carbohydrate) indicated in Table 1. In the following Examples, the amount (%) of each material to be added means the mass of each material when the mass of the solid content of the carbohydrate serving as the substrate is defined as 100%. After stirring of the respective samples, the temperature of the samples was allowed to reach 130° C. in an autoclave (manufactured by Tomy Seiko Co., Ltd., BS-325), kept at a pressure of 1.7 kgf/cm$^2$ for 3 hours, and naturally dropped to conduct a heating reaction, thereby obtaining reaction products (Reaction Products 11 to 16).

After completion of the reaction, water was added to the reaction products, and the solutions were stirred and filtered through a 0.45-μm filter (manufactured by Merck Millipore Ltd.) and a 0.22-μm filter (manufactured by Merck Millipore Ltd.). The respective samples obtained by diluting the respective filtrates with water were used as samples for HPLC analysis and samples for analysis of the degree of coloration.

(2) Analysis of 5-HMF, Fructose and Sugar Condensate by HPLC

The conditions for HPLC used in the analysis were as follows.

<HPLC Fractionation Conditions>

Column: KS-801 (8.0 mm×300 mm) (manufactured by Showa Denko K.K.)

Flow rate: 1.0 mL/min. (constant flow rate)

Detector: RI

Column temperature: 80° C.

Amount of sample to be injected: 10 μL

On the premise that the peak appearing between at 7.5 minutes and at 8.5 minutes of the retention time in the HPLC analysis corresponded to fructose and that the peak appearing between at 16.5 minutes and at 18.5 minutes of the retention time corresponded to 5-HMF, the proportions (%) of fructose and 5-HMF to the total reaction product were calculated based on the integrated value of an RI analysis value.

(3) Measurement of Degree of Coloration

The absorbances at 420 nm and 720 nm in the respective solutions prepared in the above (1) were measured with a spectrophotometer (Model U-2900, manufactured by Hitachi High-Tech Science Corporation). The concentration (Brix) of the solutions was measured with a Brix meter (manufactured by ATAGO CO., LTD., PR-201a), and the degree of coloration was determined by the following formula.

[Mathematical Formula 1]

$$\text{Degree of coloration} = \frac{\text{Absorbance at 420 nm} - \text{Absorbance at 720 nm}}{\text{Concentration (Brix)}} \times 100$$

(4) Evaluation of Reaction Vessel after Reaction

To measure the degree of production of byproducts in the respective reaction products, the byproducts attached to the respective reaction vessels used in the heating reaction in the above (1) were evaluated based on the following criteria.

A: Completely removed only by washing with water

B: Washed with water and then rubbed off, but somewhat remaining

Figure 2:
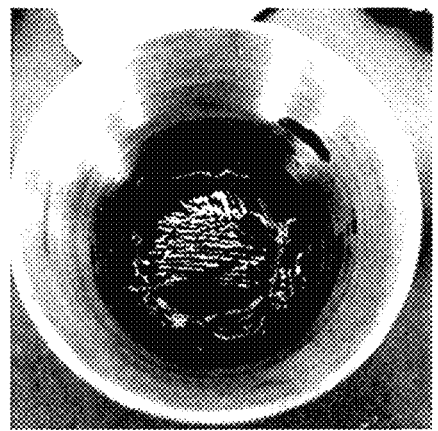
FIG. 2 is a photograph showing a state of a reaction vessel washed with water three times after a reaction using phosphoric acid as an acid catalyst (Example 1 and Reaction Product 12).
Figure 3:
FIG. 3 is a photograph showing a state of a reaction vessel washed with water three times after a reaction using an ion exchange resin as an acid catalyst (Example 1 and Reaction Product 13).
Figure 4:
FIG. 4 is a photograph showing a state of a reaction vessel washed with water three times after a reaction using hydrochloric acid as an acid catalyst and activated carbon as an agent for suppressing the production of byproducts (Example 1 and Reaction Product 14).
Figure 5:
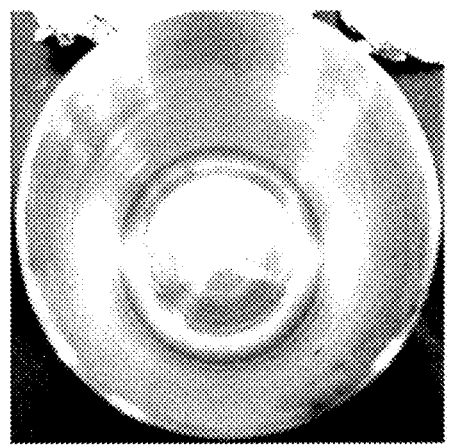
FIG. 5 is a photograph showing a state of a reaction vessel washed with water three times after a reaction using phosphoric acid as an acid catalyst and activated carbon as an agent for suppressing the production of byproducts (Example 1 and Reaction Product 15).
Figure 6:
FIG. 6 is a photograph showing a state of a reaction vessel washed with water three times after a reaction using an ion exchange resin as an acid catalyst and activated carbon as an agent for suppressing the production of byproducts (Example 1 and Reaction Product 16).

C: Washed with water and then rubbed off, but not removed at all (5) Evaluation Results The results were as indicated in Table 1. The states of the reaction vessels for Reaction Products 11 to 16 were as shown in FIGS. 1 to 6.

TABLE 1

Analysis results of reaction products obtained in the presence of various catalysts

| Reaction product | Catalyst (amount thereof added) | Agent for suppressing production of byproducts (amount thereof added) | Composition (%) *RI analysis value Fructose | 5-HMF | Degree of coloration | State of reaction vessel |
|---|---|---|---|---|---|---|
| 11 | Hydrochloric acid (0.5%) | — | 19.0 | 28.0 | 98.4 | C |
| 12 | Phosphoric acid (0.8%) | — | 31.7 | 25.7 | 72.0 | C |
| 13 | Ion exchange resin (10%) | — | 28.4 | 22.5 | 77.3 | C |
| 14 | Hydrochloric acid (0.5%) | Activated carbon 1 (20%) | 18.5 | 29.4 | 82.1 | B |
| 15 | Phosphoric acid (0.8%) | Activated carbon 1 (20%) | 29.5 | 30.3 | 11.8 | A |
| 16 | Ion exchange resin (10%) | Activated carbon 1 (20%) | 24.3 | 27.0 | 8.9 | A |

*No agent for suppressing the production of byproducts was used to produce Reaction Products 11 to 13.

From the results presented in Table 1, it was revealed that, by using activated carbon as the agent for suppressing the production of byproducts for the dehydration reaction from fructose to 5-HMF, reaction solutions containing 5-HMF with a low degree of coloration could be produced in a yield comparable to those attained when the reaction was performed using the acid catalyst alone. In particular, when phosphoric acid or an ion exchange resin was used as the acid catalyst, the degree of coloration was remarkably low. Also, it was confirmed that the use of activated carbon as the agent for suppressing the production of byproducts significantly reduced the production of a burnt deposit-like product attached to the bottom surfaces of the reaction vessels after the reaction. From the above, it was revealed that 5-HMF with a high commercial value could be produced inexpensively and simply on an industrial scale by using activated carbon as the agent for suppressing the production of byproducts for the dehydration reaction from fructose to 5-HMF.

Example 2: Production of 5-HMF Using Various Activated Carbons as Agents for Suppressing the Production of Byproducts, and Analysis Thereon (1) Preparation of Samples In the present example, high fructose syrup (fructose content per solid content: 95%; solid content concentration: 75.7%; product name: L-95; manufactured by Nihon Shokuhin Kako Co., Ltd.) was used as a substrate carbohydrate. Pure water was added to the high fructose syrup to adjust the solid content concentration thereof to 61.4%. To 10.0 g of this solution, activated carbon was added so that the amount thereof reached 0.42 g, and mixed well. This mixed solution (about 0.7 g) was weighed out into reaction vessels (made of glass), and phosphoric acid was added thereto so as to attain the amounts indicated in Table 2. The samples were each set in an autoclave (product name: RCH-1000, HIP-7518, manufactured by Tokyo Rikakikai Co., Ltd.). The temperature of the samples was allowed to reach the temperatures indicated in Table 2, kept at a pressure of 3.1 to 3.6 kgf/cm$^2$ for 60 minutes, and naturally dropped to conduct a heating reaction, thereby obtaining reaction products (Reaction Products 21 to 25). For reaction products to be produced without addition of activated carbon, reaction products were obtained in a similar manner as above, except no activated carbon was added (Reaction Products 26 and 27). After completion of the reaction, the reaction products were filtered through a 0.45-μm filter (manufactured by Merck Millipore Ltd.) and a 0.22-μm filter (manufactured by Merck Millipore Ltd.). Pure water was added to the filtered samples to attain an amount of 6.0 to 7.0 ml. The samples filtered through a 0.22-μm filter (manufactured by Merck Millipore Ltd.) were used as samples for HPLC analysis.

(2) Analysis of 5-HMF and Fructose by HPLC

The conditions for HPLC used in the analysis were as follows.

<HPLC Fractionation Conditions>

Column: KS-801 (8.0 mm×300 mm) (manufactured by Showa Denko K.K.)

Flow rate: 1.0 mL/min. (constant flow rate)

Detector: RI

Column temperature: 80° C.

Amount of sample to be injected: 10 μL

On the premise that the peak appearing between at 7.5 minutes and at 8.5 minutes of the retention time in the HPLC analysis corresponded to fructose and that the peak appearing between at 16.5 minutes and at 18.5 minutes of the retention time corresponded to 5-HMF, the proportions (%) of fructose and 5-HMF to the total reaction product were calculated based on the integrated value of an RI analysis value.

(3) Evaluation of Reaction Vessel after Reaction

To measure the degree of production of byproducts in the respective reaction products, the byproducts attached to the respective reaction vessels used in the heating reaction in the above (1) were evaluated based on the following criteria.

A: Completely removed only by washing with water

B: When washed with water and then rubbed off, somewhat removed

C: Hardly rubbed off after washing with water (4) Evaluation Results

The results were as indicated in Table 2.

TABLE 2

Analysis results of reaction products in the presence of various catalysts

| Reaction product | Catalyst (amount thereof added) | Agent for suppressing production of byproducts (amount thereof added) | Temperature (° C.) | Composition (%) *RI analysis value Fructose | 5-HMF | State of reaction vessel |
|---|---|---|---|---|---|---|
| 21 | Phosphoric acid (0.76%) | Activated carbon 1 (zinc chloride activated carbon) (6.8%) | 160 | 33.4 | 34.3 | A |

TABLE 2-continued

Analysis results of reaction products in the presence of various catalysts

| Reaction product | Catalyst (amount thereof added) | Agent for suppressing production of byproducts (amount thereof added) | Temperature (° C.) | Composition (%) *RI analysis value Fructose | 5-HMF | State of reaction vessel |
|---|---|---|---|---|---|---|
| 22 | Phosphoric acid (0.72%) | Activated carbon 2 (phosphoric acid activated carbon) (6.8%) | 160 | 17.6 | 40.1 | A |
| 23 | Phosphoric acid (0.72%) | Activated carbon 3 (stem activated carbon) (6.8%) | 160 | 28.3 | 28.0 | A |
| 24 | Phosphoric acid (0.72%) | Activated carbon 4 (phosphoric acid activated carbon) (6.8%) | 160 | 29.7 | 33.3 | A |
| 25 | Phosphoric acid (0.73%) | Activated carbon 5 (zinc chloride activated carbon) (6.8%) | 155 | 22.0 | 35.1 | A |
| 26 | Phosphoric acid (0.77%) | — | 160 | 33.8 | 32.9 | C |
| 27 | Phosphoric acid (0.69%) | | 155 | 27.3 | 26.7 | C |

*No agent for suppressing the production of byproducts was used to produce Reaction Products 26 and 27.

From the results presented in Table 2, it was revealed that, when activated carbon was used as the agent for suppressing the production of byproducts for the dehydration reaction from fructose to 5-HMF, 5-HMF could be produced whichever method was used for activation of carbon.

Example 3: Production of 5-HMF Using Organic Solvent (DMSO), and Analysis Thereon (1) Preparation of Samples In the present example, a high fructose syrup (fructose content per solid content: 95%; solid content concentration: 74.8%; product name: L-95; manufactured by Nihon Shokuhin Kako Co., Ltd.) was used as a substrate carbohydrate. Dimethyl sulfoxide (7.31 g) was added to 10.00 g of the high fructose syrup. After thorough stirring, evaporation was performed at 80° C. with an evaporator to remove water (Solution A). Thereafter, 4.00 g of Solution A was weighed out into a beaker, and well mixed with 6.00 g of dimethyl sulfoxide (Solution B). Then, about 0.5 g of Solution B was accurately weighed out into respective reaction vessels (made of glass), and activated carbon and phosphoric acid were added thereto so as to attain the amounts indicated in Table 3. The temperature of the samples was allowed to reach 150° C. in an autoclave (product name: RCH-1000, HIP-7518, manufactured by Tokyo Rikakikai Co., Ltd.), kept at a normal pressure for 70 minutes, and naturally dropped to conduct a heating reaction, thereby obtaining reaction products (Reaction Products 31 and 32). After completion of the reaction, the samples were each transferred to a 200-ml eggplant-shaped flask while they were washed with pure water, and subjected to evaporation at 120° C. for 30 minutes with an evaporator. Pure water was added again for dissolution, and the solutions were filtered through a 0.45-μm filter (manufactured by Merck Millipore Ltd.) and a 0.22-μm filter (manufactured by Merck Millipore Ltd.) which were weighed in advance. Pure water was used to recover all the soluble reaction products remaining in the filters. Thereafter, the filters were dried at 105° C. overnight, and the mass of the solid matter attached to the filters was determined. The proportion of the mass of the solid matter to the mass of the solid content of the substrate carbohydrate subjected to the reaction was calculated as the mass rate (%) of the solid matter in the respective reaction products. The liquid amount (mL) of the respective filtered samples was measured, and 99 μL out of the amount was subjected to HPLC analysis.

(2) Analysis of 5-HMF by HPLC

The conditions for HPLC used in the analysis were as follows.

<HPLC Fractionation Conditions>

Column: KS-801 (8.0 mm×300 mm) (manufactured by Showa Denko K.K.)

Flow rate: 1.0 mL/min. (constant flow rate)

Detector: RI

Column temperature: 80° C.

On the premise that the peak appearing between at 16.5 minutes and at 18.5 minutes of the retention time for the HPLC analysis corresponded to 5-HMF, the integrated value of an RI analysis value was determined. The molar yield (%) of 5-HMF to the raw material carbohydrate was calculated based on the calibration curve of the RI integrated value and the 5-HMF mass preliminarily obtained from a preparation of 5-HMF.

(3) Evaluation Results

The results were as indicated in Table 3.

TABLE 3

Analysis results of reaction products in the presence of various catalysts

| Reaction product | Catalyst (amount thereof added) | Agent for suppressing production of byproducts (amount thereof added) | Molar yield (%) of 5-HMF | Mass rate (%) of solid matter in reaction product |
|---|---|---|---|---|
| 31 | Phosphoric acid (0.70%) | Activated carbon 1 (zinc chloride activated carbon) (0%) | 13.1 | 19.2 |

TABLE 3-continued

Analysis results of reaction products in the presence of various catalysts

| Reaction product | Catalyst (amount thereof added) | Agent for suppressing production of byproducts (amount thereof added) | Molar yield (%) of 5-HMF | Mass rate (%) of solid matter in reaction product |
|---|---|---|---|---|
| 32 | Phosphoric acid (0.71%) | Activated carbon 1 (zinc chloride activated carbon) (5%) | 27.9 | 2.8 |

From the results presented in Table 3, it was revealed that 5-HMF could be produced also when an organic solvent was used as a solvent in the case where activated carbon was used as the agent for suppressing the production of byproducts to synthesize 5-HMF. Also, it was revealed that the use of activated carbon as the agent for suppressing the production of byproducts provided a higher yield of 5-HMF and less solid matter produced as byproducts.

Example 4: Production of 5-HMF Using Phosphoric Acid and Activated Carbon, and Analysis Thereon (1) Preparation of Samples 400 mg of activated carbon 1 (zinc chloride activated carbon) and activated carbon 6 (steam activated carbon) were weighed out into respective sample tubes, and 20 mL of a 1M aqueous phosphoric acid solution was added to the respective sample tubes, and stirred in a rotary mixer for 4 days. After stirring, the solutions were filtered through a 0.45-µm filter (manufactured by Toyo Roshi Kaisha, Ltd.) to recover activated carbons. The recovered activated carbons were washed off with ultrapure water and dried at 105° C. This treatment provides activated carbons having phosphoric acid adsorbed thereon or having a modified phosphoric acid group. In the present example, the thus activated carbons are referred to as activated carbon 1P (obtained using activated carbon 1 as a raw material) and activated carbon 6P (obtained using activated carbon 6 as a raw material), respectively.

In the present example, a high fructose syrup (fructose content per solid content: 95%; solid content concentration: 75.7%; product name: L-95; manufactured by Nihon Shokuhin Kako Co., Ltd.) was used as a substrate carbohydrate. Pure water was added to the high fructose syrup to adjust the solid content concentration thereof to 61.4%. The activated carbons were each added so as to attain the amounts indicated in Table 4, and 0.5 mL of the mixed solutions were accurately weighed out into reaction vessels (made of glass), and phosphoric acid was added thereto so as to attain the amounts indicated in Table 4. The samples were each set in an autoclave (product name: RCH-1000, HIP-7518, manufactured by Tokyo Rikakikai Co., Ltd.). The temperature of the samples was allowed to reach the temperatures indicated in Table 4, kept at a pressure of 2.7 to 3.5 kgf/cm² for 60 minutes, and naturally dropped to conduct a heating reaction, thereby obtaining reaction products (Reaction Products 41 and 42). For reaction products to be produced without addition of activated carbon, reaction products were obtained in a similar manner as above, except no activated carbon was added (Reaction Products 43 and 44). After completion of the reaction, the reaction products were filtered through a 0.45-µm filter (manufactured by Merck Millipore Ltd.) and a 0.22-µm filter (manufactured by Merck Millipore Ltd.). Pure water was added to the filtered samples to attain an amount of 6.0 mL. The samples filtered through a 0.22-µm filter (manufactured by Merck Millipore Ltd.) were used as samples for HPLC analysis. The liquid amount (mL) of the respective filtered samples was measured, and 10 µL out of the amount was subjected to HPLC analysis.

(2) Analysis of 5-HMF by HPLC

The conditions for HPLC used in the analysis were as follows.

<HPLC Fractionation Conditions>

Column: KS-801 (8.0 mm×300 mm) (manufactured by Showa Denko K.K.)

Flow rate: 1.0 mL/min. (constant flow rate)

Detector: RI

Column temperature: 80° C.

On the premise that the peak appearing between at 16.5 minutes and at 18.5 minutes of the retention time for the HPLC analysis corresponded to 5-HMF, the integrated value of an RI analysis value was determined. The molar yield (%) of 5-HMF to the raw material carbohydrate was calculated based on the calibration curve of the RI integrated value and the 5-HMF mass preliminarily obtained from a preparation of 5-HMF.

(3) Evaluation of Reaction Vessel after Reaction

To measure the degree of production of byproducts in the respective reaction products, the byproducts attached to the respective reaction vessels used in the heating reaction in the above (1) were evaluated based on the following criteria.

A: Completely removed only by washing with water

B: When washed with water and then rubbed off, somewhat removed

C: Hardly rubbed off after washing with water (4) Evaluation Results

The results were as indicated in Table 4.

TABLE 4

Analysis results of reaction products in the presence of various catalysts

| Reaction product | Reaction temperature (° C.) | Catalyst (amount thereof added) | Agent for suppressing production of byproducts (amount thereof added) | Molar yield (%) of 5-HMF | State of reaction vessel |
|---|---|---|---|---|---|
| 41 | 155 | Phosphoric acid (0%) | Activated carbon 1P (steam activated carbon) (20%) | 25.8 | A |

TABLE 4-continued

Analysis results of reaction products in the presence of various catalysts

| Reaction product | Reaction temperature (° C.) | Catalyst (amount thereof added) | Agent for suppressing production of byproducts (amount thereof added) | Molar yield (%) of 5-HMF | State of reaction vessel |
|---|---|---|---|---|---|
| 42 | 160 | Phosphoric acid (0.76%) | Activated carbon 6P (zinc chloride activated carbon) (7%) | 32.6 | A |
| 43 | 155 | Phosphoric acid (0.69%) | — | 26.9 | C |
| 44 | 160 | Phosphoric acid (0.77%) | — | 34.0 | C |

*No agent for suppressing the production of byproducts was used to produce Reaction Products 43 and 44.

From the results presented in Table 4, it was revealed that, in the case where phosphoric acid was used as the catalyst for the dehydration reaction from fructose to 5-HMF, and activated carbon was used as the agent for suppressing the production of byproducts, 5-HMF could be produced also when activated carbon preliminarily immersed in an aqueous phosphoric acid solution was used. Also, it was revealed that 5-HMF could be produced also when activated carbon preliminarily immersed in an aqueous phosphoric acid solution was used in combination with phosphoric acid. It was found that, in this case, the attachment of byproducts to the reaction vessels could be prevented with almost no change in yield of 5-HMF, as compared with the case where 5-HMF was produced using phosphoric acid.

Example 5: Production of 5-HMF Using Various Materials as Agents for Suppressing the Production of Byproducts, and Analysis Thereon (1) Preparation of Samples In the present example, a high fructose syrup (fructose content per solid content: 95%; solid content concentration: 75.7%; product name: L-95; manufactured by Nihon Shokuhin Kako Co., Ltd.) was used as a substrate carbohydrate. Pure water was added to the high fructose syrup to adjust the solid content concentration thereof to 61.4%. To 10.0 g of this solution, an agent for suppressing the production of byproducts was added so that the amount thereof reached 0.42 g, and mixed well. This mixed solution (about 0.7 g) was weighed out into a reaction vessel (made of glass), and phosphoric acid was added thereto so as to attain the amounts indicated in Table 5. The samples were each set in an autoclave (product name: RCH-1000, HIP-7518, manufactured by Tokyo Rikakikai Co., Ltd.). The temperature of the samples was allowed to reach the temperature indicated in Table 5, kept at a pressure of 3.1 to 3.6 kgf/cm$^2$ for 60 minutes, and naturally dropped to conduct a heating reaction, thereby obtaining reaction products (Reaction Products 51 and 52). For a reaction product to be produced without addition of activated carbon, a reaction product was obtained in a similar manner as above, except no activated carbon was added (Reaction Product 53). After completion of the reaction, the reaction products were filtered through a 0.45-nm filter (manufactured by Merck Millipore Ltd.) and a 0.22-nm filter (manufactured by Merck Millipore Ltd.). Pure water was added to the filtered samples to attain an amount of 6.0 to 7.0 ml. The samples filtered through a 0.22-nm filter (manufactured by Merck Millipore Ltd.) were used as samples for HPLC analysis.

(2) Analysis of 5-HMF and Fructose by HPLC

The conditions for HPLC used in the analysis were as follows.

<HPLC Fractionation Conditions>

Column: KS-801 (8.0 mm×300 mm) (manufactured by Showa Denko K.K.)

Flow rate: 1.0 mL/min. (constant flow rate)

Detector: RI

Column temperature: 80° C.

Amount of sample to be injected: 10 μL

On the premise that the peak appearing between at 7.5 minutes and at 8.5 minutes of the retention time in the HPLC analysis corresponded to fructose and that the peak appearing between at 16.5 minutes and at 18.5 minutes of the retention time corresponded to 5-HMF, the proportions (%) of fructose and 5-HMF to the total reaction product were calculated based on the integrated value of an RI analysis value.

(3) Evaluation of Reaction Vessel after Reaction

To measure the degree of production of byproducts in the respective reaction products, the byproducts attached to the respective reaction vessels used in the heating reaction in the above (1) were evaluated based on the following criteria.

A: Completely removed only by washing with water
B: When washed with water and then rubbed off, somewhat removed
C: Hardly rubbed off after washing with water (4) Evaluation Results The results were as indicated in Table 5.

TABLE 5

Analysis results of reaction products in the presence of various catalysts

| Reaction product | Catalyst (amount thereof added) | Agent for suppressing production of byproducts (amount thereof added) | Temperature (° C.) | Composition (%) *RI analysis value | | State of reaction vessel |
|---|---|---|---|---|---|---|
| | | | | Fructose | 5-HMF | |
| 51 | Phosphoric acid (0.74%) | Activated carbon 7 (coal-derived) (6.8%) | 155 | 37.9 | 17.0 | A |

TABLE 5-continued

Analysis results of reaction products in the presence of various catalysts

| Reaction product | Catalyst (amount thereof added) | Agent for suppressing production of byproducts (amount thereof added) | Temperature (° C.) | Composition (%) *RI analysis value | | State of reaction vessel |
|---|---|---|---|---|---|---|
| | | | | Fructose | 5-HMF | |
| 52 | Phosphoric acid (0.72%) | Activated carbon 8 (graphite) (6.8%) | 155 | 32.5 | 26.8 | A |
| 53 | Phosphoric acid (0.69%) | — | 155 | 27.3 | 26.7 | C |

*No agent for suppressing the production of byproducts was used to produce Reaction Product 53.

From the results presented in Table 5, it was revealed that 5-HMF could be produced also when coal-derived activated carbon and graphite were each used as the agent for suppressing the production of byproducts for the dehydration reaction from fructose to 5-HMF.

Example 6: Production of 5-HMF from Various Raw Material Carbohydrates, and Analysis Thereon (1) Preparation of Samples In the present example, glucose (manufactured by Kanto Chemical Co., Inc.), inulin (manufactured by Fuji Nihon Seito Corporation) and corn starch (manufactured by Nihon Shokuhin Kako Co., Ltd.) were used as substrate carbohydrates. The respective substrate carbohydrates (10.0 g, each powdered product) were put in respective reaction vessels (made of glass). For reaction products to be produced with addition of activated carbon, 0.5 g of activated carbon was added. To these, 90.0 g of distilled water and phosphoric acid were added so as to attain the amount indicated in Table 6, and the respective samples were stirred and then programmed as follows and heated in an autoclave (product name: CPP-2000, manufactured by Sibata Scientific Technology, Ltd.). Thereafter, the temperature of the samples was naturally dropped to conduct a heating reaction, thereby obtaining reaction products (Reaction Products 61 to 66). After completion of the reaction, the samples filtered through a 0.22-μm filter (manufactured by Merck Millipore Ltd.) were used as samples for HPLC analysis.

(2) Analysis of 5-HMF and Monosaccharide by HPLC

The conditions for HPLC used in the analysis were as follows.

<HPLC Fractionation Conditions>

Column: KS-801 (8.0 mm×300 mm) (manufactured by Showa Denko K.K.)
Flow rate: 1.0 mL/min. (constant flow rate)
Detector: RI
Column temperature: 80° C.
Amount of sample to be injected: 50 μL On the premise that the peak appearing between at 7.0 minutes and at 8.5 minutes of the retention time in the HPLC analysis corresponded to monosaccharide and that the peak appearing between at 16.5 minutes and at 18.5 minutes of the retention time corresponded to 5-HMF, the proportions (%) of various raw material carbohydrates and 5-HMF to the total reaction product were calculated based on the integrated value of an RI analysis value.

(3) Evaluation of Reaction Vessel after Reaction

To measure the degree of production of byproducts in the respective reaction products, the byproducts attached to the respective reaction vessels used in the heating reaction in the above (1) were evaluated based on the following criteria.
A: Completely removed only by washing with water
B: When washed with water and then rubbed off, somewhat removed
C: Hardly rubbed off after washing with water (4) Evaluation Results The results were as indicated in Table 6.

TABLE 6

Analysis results of reaction products obtained in the presence of various catalysts

| Reaction product | Substrate | Reaction condition | Catalyst (amount thereof added) | Agent for suppressing production of byproducts (amount thereof added) | Composition (%) *RI analysis value | | State of reaction vessel |
|---|---|---|---|---|---|---|---|
| | | | | | Monosaccharide | 5-HMF | |
| 61 | Cornstarch | Heater was heated up to 185° C. within 50 min. and kept for 3 hr., | Phosphoric acid (0.72%) | Activated carbon 1 (5%) | 78.5 | 7.8 | A |
| 62 | | | Phosphoric acid (0.72%) | — | 82.1 | 6.2 | C |
| 63 | Glucose | and then temperature was naturally dropped. | Phosphoric acid (0.72%) | Activated carbon 1 (7%) | 81.0 | 6.4 | A |
| 64 | | | Phosphoric acid (0.72%) | — | 79.6 | 6.7 | B |
| 65 | Inulin | Heater was heated up to 174° C. within 50 min. and kept for 1 hr., and then temperature was naturally dropped. | Phosphoric acid (0.72%) | Activated carbon 1 (7%) | 48.6 | 35.3 | A |
| 66 | | | Phosphoric acid (0.72%) | — | 48.0 | 34.8 | C |

*No agent for suppressing the production of byproducts was used to produce Reaction Products 62, 64 and 66.

From the results presented in Table 6, it was revealed that 5-HMF could be produced also when various hexoses other than fructose and various sugar polymers each comprising a hexose as a constituent sugar were used as the substrate carbohydrates for synthesizing 5-HMF using activated carbon as the agent for suppressing the production of byproducts. Also, it was confirmed that the use of activated carbon as the agent for suppressing the production of byproducts suppressed the attachment of byproducts to the reaction vessels whichever substrate was used.

Example 7: Production of 5-HMF when Using Fructose Solutions Having Various Concentrations as Substrates and Activated Carbon as Agent for Suppressing the Production of Byproducts, and Analysis Thereon (1) Preparation of Samples In the present example, fructose (manufactured by Nacalai Tesque, Inc.) was used as a substrate carbohydrate. To a fructose solution prepared by dissolving fructose in pure water, hydrochloric acid (manufactured by Nacalai Tesque, Inc.) was added to adjust the concentration of the fructose solution to the values indicated in Table 7. The solutions (1.2 mL) were weighed out into respective reaction vessels (made of glass). For reaction products to be produced with addition of activated carbon, activated carbon was added to the respective solutions in the amount indicated in Table 7. The samples were each set in an autoclave (product name: RCH-1000, HIP-7518, manufactured by Tokyo Rikakikai Co., Ltd.). The temperature of the samples was allowed to reach the temperature indicated in Table 7, and kept for the times indicated in this table to conduct a heating reaction, thereby obtaining reaction products (Reaction Products 71 to 80). The reaction products were each filtered through a 0.22-μm filter (manufactured by Merck Millipore Ltd.). Pure water was used to recover all the soluble reaction products remaining in the filter. The recovered filtrates (1 mL) were each applied to a syringe charged with about 2 mL of an ion exchange resin MB-4 (manufactured by ORGANO CORPORATION). Pure water was used to recover 10 mL of purified solutions which were used as samples for HPLC analysis.

(2) Analysis of 5-HMF by HPLC

The conditions for HPLC used in the analysis were as follows.

<HPLC Fractionation Conditions>

Column: KS-801 (8.0 mm×300 mm) (manufactured by Showa Denko K.K.)
Flow rate: 1.0 mL/min. (constant flow rate)
Detector: RI
Column temperature: 80° C.
Amount of sample to be injected: 90 μL On the premise that the peak appearing between at 16.5 minutes and at 18.5 minutes of the retention time for the HPLC analysis corresponded to 5-HMF, the integrated value of an RI analysis value was determined. The molar yield (%) of 5-HMF to the raw material carbohydrate was calculated based on the calibration curve of the RI integrated value and the 5-HMF mass preliminarily obtained from a preparation of 5-HMF.

(3) Evaluation of Reaction Vessel after Reaction

To measure the degree of production of byproducts in the respective reaction products, the byproducts attached to the respective reaction vessels used in the heating reaction in the above (1) were evaluated based on the following criteria.

A: Completely removed only by washing with water
B: When washed with water and then rubbed off, somewhat removed
C: Hardly rubbed off after washing with water (4) Evaluation Results The results were as indicated in Table 7.

TABLE 7

Analysis results of reaction products obtained at various substrate concentrations

| Reaction product | Fructose concentration (%) | Reaction condition | Catalyst (amount thereof added) | Agent for suppressing production of byproducts (amount thereof added) | Molar yield (%) of 5-HMF | State of reaction vessel |
|---|---|---|---|---|---|---|
| 71 | 6 | Heater was heated up to 90° C. within 20 min. and kept for 7 hr. | Hydrochloric acid (3.6%) | — | 16.5 | A |
| 72 | 12 | | Hydrochloric acid (3.6%) | — | 10.9 | A |
| 73 | 19 | Heater was heated up to 90° C. within 20 min. and kept for 5 hr. | Hydrochloric acid (3.6%) | — | 12.6 | B |
| 74 | 19 | | Hydrochloric acid (3.6%) | Activated carbon 1 (3.8%) | 12.0 | A |
| 75 | 24 | Heater was heated up to 90° C. within 20 min. and kept for 4 hr. | Hydrochloric acid (3.6%) | — | 13.1 | C |
| 76 | 24 | | Hydrochloric acid (3.6%) | Activated carbon 1 (3.8%) | 13.9 | A |
| 77 | 35 | | Hydrochloric acid (3.6%) | — | 11.6 | C |
| 78 | 35 | | Hydrochloric acid (3.6%) | Activated carbon 1 (3.8%) | 12.9 | A |
| 79 | 53 | Heater was heated up to 90° C. within 20 min. and kept for 3 hr. | Hydrochloric acid (3.6%) | — | 7.6 | C |
| 80 | 53 | | Hydrochloric acid (3.6%) | Activated carbon 1 (3.8%) | 10.2 | A |

*No agent for suppressing the production of byproducts was used to produce Reaction Products 71, 72, 73, 75, 77 and 79.

From the results indicated in Table 7, it was found that burning occurred in the tested products having a fructose concentration of 19% or more under the conditions. Also, it was revealed that 5-HMF could be produced when activated carbon was used as the agent for suppressing the production of byproducts, in all the tested products in which burning occurred. Further, it was confirmed that the use of activated carbon as the agent for suppressing the production of byproducts suppressed the attachment of byproducts to the reaction vessels whichever concentration was employed.

The invention claimed is:

1. A method for suppressing the production of byproducts in a reaction for producing 5-hydroxymethyl-2-furfural, through a dehydration reaction, from a carbohydrate comprising a hexose as a constituent sugar or a derivative thereof, wherein the dehydration reaction is performed in the presence of activated carbon.

2. The method for suppressing the production of byproducts according to claim 1, wherein the carbohydrate or derivative thereof has a solid content concentration of 15% by mass or more.

3. The method for suppressing the production of byproducts according to claim 1, wherein the dehydration reaction is a reaction using an acid catalyst.

* * * * *